United States Patent
Sun et al.

(10) Patent No.: US 11,111,191 B2
(45) Date of Patent: Sep. 7, 2021

(54) METHOD FOR PREPARING HEXADECAHYDROPYRENE

(71) Applicants: China Petroleum & Chemical Corporation, Beijing (CN); Fushun Research Institute of Petroleum and Petrochemicals, SINOPEC CORP., Liaoning (CN)

(72) Inventors: Guoquan Sun, Liaoning (CN); Xiangchen Fang, Liaoning (CN); Hongfei Fan, Liaoning (CN); Chunlei Yao, Liaoning (CN); Hui Quan, Liaoning (CN)

(73) Assignees: CHINA PETROLEUM & CHEMICAL CORPORATION, Beijing (CN); FUSHUN RESEARCH INSTITUTE OF PETROLEUM AND PETROCHEMICALS, SINOPEC CORP., Liaoning (CN)

( * ) Notice: Subject to any disclaimer, the term of this patent is extended or adjusted under 35 U.S.C. 154(b) by 17 days.

(21) Appl. No.: 16/464,405

(22) PCT Filed: Nov. 30, 2017

(86) PCT No.: PCT/CN2017/113834
§ 371 (c)(1),
(2) Date: May 28, 2019

(87) PCT Pub. No.: WO2018/099419
PCT Pub. Date: Jun. 7, 2018

(65) Prior Publication Data
US 2020/0262769 A1     Aug. 20, 2020

(30) Foreign Application Priority Data

Nov. 30, 2016  (CN) .......................... 201611083230.4
Nov. 30, 2016  (CN) .......................... 201611084897.6

(51) Int. Cl.
*C07C 5/10* (2006.01)
*C07C 13/66* (2006.01)

(52) U.S. Cl.
CPC .............. *C07C 5/10* (2013.01); *C07C 13/66* (2013.01); *C07C 2523/44* (2013.01); *C07C 2529/08* (2013.01)

(58) Field of Classification Search
None
See application file for complete search history.

(56) References Cited

U.S. PATENT DOCUMENTS 3,151,055 A * 9/1964 Muller ...................... C10C 1/02
208/39
3,303,227 A * 2/1967 Schneider ............. C07C 5/2721
585/21

(Continued)

FOREIGN PATENT DOCUMENTS

| CN | 1351130 A | 5/2002 |
| CN | 1415704 A | 5/2003 |

(Continued)

OTHER PUBLICATIONS

Machine translation CN104588073A. May 6, 2015 (Year: 2015).*

(Continued)

*Primary Examiner* — Philip Y Louie
*Assistant Examiner* — Alyssa L Cepluch
(74) *Attorney, Agent, or Firm* — Novick, Kim & Lee, PLLC; Allen Xue (57) ABSTRACT

A method for preparing hexadecahydropyrene includes the step of carrying out the hydrogenation reaction to hydrocarbon oil containing pyrene compounds in the presence of a hydrogenation catalyst. The pyrene compounds are selected from at least one of pyrene and unsaturated hydrogenation products thereof. The hydrogenation catalyst contains a (Continued)

carrier and an active metal component loaded on the carrier. The active metal component is Pt and/or Pd and the carrier contains a small crystal size Y zeolite, alumina and amorphous silica-alumina. The small crystal size Y zeolite has an average grain diameter of 200-700 nm, a molar ratio of $SiO_2$ to $Al_2O_3$ of 40-120, a relative crystallinity of ≥95%, and a specific surface area of 900-1,200 m$^2$/g. The pore volume of secondary pores in 1.7-10 nm diameter is more than 50% of the total pore volume.

22 Claims, 1 Drawing Sheet

(56) References Cited

U.S. PATENT DOCUMENTS

| | | | |
|---|---|---|---|
| 3,409,684 A | 11/1968 | Aristoff et al. | |
| 3,709,814 A * | 1/1973 | Jaffe | C10G 65/10 502/66 |
| 5,030,780 A | 7/1991 | Ward et al. | |
| 7,351,395 B1 | 4/2008 | Pez et al. | |
| 2016/0115401 A1 | 4/2016 | Xu et al. | |
| 2017/0283717 A1 * | 10/2017 | Dandekar | C10G 69/02 |

FOREIGN PATENT DOCUMENTS

| | | | |
|---|---|---|---|
| CN | 1676583 A | | 10/2005 |
| CN | 101759198 A | * | 6/2010 |
| CN | 103666553 A | | 3/2014 |
| CN | 104588073 A | * | 5/2015 |
| CN | 104588073 A | | 5/2015 |
| CN | 104646052 A | | 5/2015 |
| CN | 104910953 A | | 9/2015 |
| JP | S61-103988 A | | 5/1986 |
| RU | 2275397 C1 | | 4/2006 |

OTHER PUBLICATIONS

Machine translation CN101759198A. Jun. 30, 2010 (Year: 2010).*
ECHA "Distillates (petroleum), vacuum" Registration Dossier, pp. 1-46. 2011 (Year: 2011).*
ECHA "Distillates (coal tar), high-temperature, heavy oils" Registration Dossier, pp. 1-6. 2018 (Year: 2018).*
ECHA "Distillates (coal tar), heavy oils" Brief Profile, pp. 1-11. 2011 (Year: 2011).*
Xiangchun Meng et al:"Tailoring the pore size of zeolite Y as the support of diesel aromatic saturation catalyst", J Porous Mater (2006) vol. 13, pp. 365-371, Aug. 2006.
Kamiya, Yoshio; "Coal Liguefacion", vol. 71, Issue. 2, Feb. 1, 1985, pp. 157-163, Iron to steel, Online ISSN : 1883-2954, Print ISSN : 0021-157, publisher: The Iron and Steel Institute of Japan.

* cited by examiner

METHOD FOR PREPARING HEXADECAHYDROPYRENE

FIELD OF THE INVENTION

The present invention relates to a method for preparing hexadecahydropyrene.

BACKGROUND OF THE INVENTION

High-purity hexadecahydropyrene involves demanding production process and high price. Therefore, high-purity hexadecahydropyrene products meeting the market requirement become a scarce resource.

At present, a synthesis method is one of important approaches for producing high-purity hexadecahydropyrene. Pyrene is an important component of coal tar. It is enriched in the fraction of 300-360° C. during the prefractionation of coal tar, and then can be obtained by conventional methods such as rectification and crystallization, etc. The coal tar raw material essentially doesn't contain hexadecahydropyrene. There is no report on direct extraction of hexadecahydropyrene from coal tar yet, because the operation cost is high, and the extracted hexadecahydropyrene has low purity and low yield, such an approach is infeasible economically. 1,2,3,6,7,8-hexahydropyrene is usually prepared by selective catalytic hydrogenation of pyrene, since the consecutive reactions and parallel reactions are carried out simultaneously, it is difficult to improve the selectivity for a single product and more difficult to obtain high-purity hexadecahydropyrene.

The patent document CN1351130A discloses a method for producing diesel oil by coal tar hydrogenation, which mainly comprises fractionating coal tar and then hydrofining the obtained fractions below diesel oil. The method can be used to directly produce diesel oil that meets fuel oil criteria or produce blending components as diesel products. However, the method only achieve hydrotreating of the lighter fractions of coal tar, cannot extract hexadecahydropyrene product that has high added value and high-purity, and does not fully utilize coal tar.

The patent document CN1676583A discloses a hydrocracking process for medium-temperature or high-temperature coal tar. The process as follows: medium-temperature or high-temperature coal tar is heated in a heating furnace to 250-300° C., mixed with hydrogen and enters a hydrofining reactor to produce refined oil, the refined oil is fractionated in a distillation apparatus into gasoline, diesel oil, lubricant, and hydrogenation tail oil, the hydrogenation tail oil is heated in a cracking heating furnace, then mixed with hydrogen and enters a cracking reactor to further produce gasoline and diesel distillates. However, the distillates cannot be used to extract hexadecahydropyrene product directly, but only to produce blended fuel oils.

The process of coal tar directly entering the high-temperature heating furnace will cause the furnace tube to coke, affecting the normal operation cycle of the device.

SUMMARY OF THE INVENTION

The object of the present invention is to provide a method for producing hexadecahydropyrene, by which a high-purity hexadecahydropyrene product can be prepared.

Though a great deal of researches have been made on hydrogenation of coarse pyrene in the prior art, usually only hexahydropyrene can be obtained, and there is no record on obtaining hexadecahydropyrene in those researches. The inventors of the present invention have found accidentally in the research that a small crystal size Y zeolite having a high silica-alumina ratio, high crystallinity, a large quantity of secondary pores, and a large specific surface area combined with the amorphous silica-alumina and the active metal components Pt and Pd in hydrogenation catalysts can achieve full hydrogenation of the coarse pyrene raw material (hydrocarbon oil raw material that contains pyrene compounds), and the catalysts have high catalytic activity, selectivity and stability, thereby completing the present invention.

The present invention provides a method for preparing hexadecahydropyrene, which comprises controlling a hydrocarbon oil raw material that contains pyrene compounds to have a hydrogenation reaction in the presence of a hydrogenation catalyst, wherein the pyrene compounds are selected from at least one of pyrene and unsaturated hydrogenation products thereof, the hydrogenation catalyst contains a carrier and an active metal component loaded on the carrier, the active metal component is Pt and/or Pd, the carrier contains a small crystal size Y zeolite, alumina and amorphous silica-alumina, the small crystal size Y zeolite has an average grain diameter of 200-700 nm, a molar ratio of $SiO_2$ to $Al_2O_3$ of 40-120, a relative crystallinity of ≥95%, a specific surface area of 900-1,200 $m^2/g$, the pore volume of secondary pores in 1.7-10 nm diameter accounts for more than 50% of the total pore volume.

A high-purity hexadecahydropyrene product can be produced by the method for preparing hexadecahydropyrene in the present invention.

DETAILED DESCRIPTION OF THE EMBODIMENTS

The ends points and any values in the ranges disclosed herein are not limited to the exact ranges or values; instead, those ranges or values shall be comprehended as encompassing values that are close to those ranges or values. For numeric ranges, the end points of the ranges, the end points of the ranges and the discrete point values, and the discrete point values may be combined to obtain one or more new numeric ranges, which shall be deemed as having been disclosed specifically herein.

The method for preparing hexadecahydropyrene in the present invention comprises controlling a hydrocarbon oil raw material that contains pyrene compounds to have a hydrogenation reaction in the presence of a hydrogenation catalyst.

In the present invention, the said hydrogenation catalyst contains a carrier and an active metal component loaded on the carrier. The active metal component is Pt and/or Pd. The carrier contains small crystal size Y zeolite, alumina and amorphous silica-alumina.

The average grain diameter of the small crystal size Y zeolite is 200-700 nm; specifically, for example, the average grain diameter may be 200 nm, 250 nm, 300 nm, 350 nm, 400 nm, 450 nm, 500 nm, 550 nm, 600 nm, 650 nm, 700 nm, and any value within a range formed by any two of those point values. Preferably, the average grain diameter of the small crystal size Y zeolite is 300-500 nm. In the present invention, the average grain diameter of the small crystal size Y zeolite is measured by means of Scanning Electron Microscopy (SEM).

The molar ratio of $SiO_2/Al_2O_3$ in the small crystal size Y zeolite is 40-120; specifically, for example, the molar ratio may be 40, 50, 60, 70, 80, 90, 100, 110, 120, and any value within a range formed by any two of those point values.

The relatively crystallinity of the small crystal size Y zeolite is ≥95%, preferably 95-120%, more preferably 98-115%. In the present invention, the relative crystallinity of the small crystal size Y zeolite is detected with an X-ray diffraction method.

The specific surface area of the small crystal size Y zeolite may be 900-1,200 $m^2/g$; specifically, for example, the specific surface area may be 900 $m^2/g$, 920 $m^2/g$, 950 $m^2/g$, 980 $m^2/g$, 1,000 $m^2/g$, 1,020 $m^2/g$, 1,050 $m^2/g$, 1,080 $m^2/g$, 1,100 $m^2/g$, 1,120 $m^2/g$, 1,150 $m^2/g$, 1,180 $m^2/g$, 1,200 $m^2/g$, and any value within a range formed by any two of those point values. In the present invention, the specific surface area of the small crystal size Y zeolite is detected with a cryogenic liquid nitrogen physical adsorption method.

The small crystal size Y zeolite has a large quantity of secondary pores; specifically, in the small crystal size Y zeolite, the pore volume of secondary pores in 1.7-10 nm accounts for 50% or more of the total pore volume, preferably 50-80%, further preferably 60-80%. In the present invention, the pore volume of secondary pores of the small crystal size Y zeolite is detected with a cryogenic liquid nitrogen physical adsorption method.

The lattice constant of the small crystal size Y zeolite may be 2.425-2.435 nm, such as 2.425 nm, 2.426 nm, 2.427 nm, 2.428 nm, 2.429 nm, 2.43 nm, 2.431 nm, 2.432 nm, 2.433 nm, 2.434 nm, 2.435 nm, and any value within a range formed by any two of those point values. In the present invention, the lattice constant of the small crystal size Y zeolite is detected with an X-ray diffraction method.

The pore volume of the small crystal size Y zeolite may be 0.5-0.8 mL/g, such as 0.5 mL/g, 0.55 mL/g, 0.6 mL/g, 0.65 mL/g, 0.7 mL/g, 0.75 mL/g, 0.8 mL/g, and any value within a range formed by any two of those point values. In the present invention, the pore volume of the small crystal size Y zeolite is detected with a cryogenic liquid nitrogen physical adsorption method.

In the present invention, the properties of the hydrogenation catalyst are as follows: the specific surface area may be 350-550 $m^2/g$, preferably 380-500 $m^2/g$; the pore volume may be 0.5-1 mL/g, preferably 0.5-0.9 mL/g.

In the hydrogenation catalyst, based on the total weight of the hydrogenation catalyst, the content of the active metal component may be 0.1-2 wt %, preferably 0.2-1.5 wt %; the content of the carrier may be 98-99.9 wt %, preferably 98.5-99.8 wt %.

In the carrier, based on the total weight of the carrier, the content of the small crystal size Y zeolite may be 5-40 wt %, preferably 10-25 wt %; the content of the alumina may be 10-40 wt %, preferably 15-30 wt %; the content of the amorphous silica-alumina may be 20-65 wt %, preferably 30-60 wt %.

In the present invention, the hydrogenation catalyst may be selected from an appropriate commercial catalyst, or may be prepared by a conventional method in the art, for example, according to the method reported in the patent document CN104588073A. Specifically, the preparation method of the hydrogenation catalyst may comprise: mixing the small crystal size Y zeolite, the amorphous silica-alumina, and a binder made of alumina mechanically and forming, and then drying and calcining to produce a catalyst carrier; loading Pt and/or Pd on the carrier by impregnation method, and then drying and calcining to obtain the hydrogenation catalyst.

The preparation method of the small crystal size Y zeolite may comprise the following steps:

(1) producing small crystal size NaY zeolite into small crystal size $NH_4NaY$ zeolite with $Na_2O$ content ≤2.5 wt %;

(2) treating the small crystal size $NH_4NaY$ zeolite by hydrothermal treatment, and then using ammonium hexafluorosilicate solution to carry out dealumination and silicon reinsertion;

(3) treating the zeolite obtained in the step (2) with mixed solution that contains $NH_4^+$ and $H^+$, and then washing and drying, to obtain small crystal size Y zeolite.

The properties of the small crystal size NaY zeolite are as follows: the molar ratio of $SiO_2/Al_2O_3$ is greater than 6 and not greater than 9, preferably 6.5-9, further preferably 7-8; the average grain diameter is 200-700 nm, preferably 300-500 nm; the specific surface area is 800-1,000 $m^2/g$, preferably 850-950 $m^2/g$; the pore volume is 0.3-0.45 mL/g, the relative crystallinity is 90-130%, the lattice constant is 2.46-2.47, the relative crystallinity after calcination in air at 650° C. for 3 h is 90% or higher, preferably 90-110%, more preferably 90-105%.

According to a preferred embodiment of the present invention, the hydrogenation reaction process includes two stages of reaction that are executed sequentially; correspondingly, the catalyst used in the first stage of reaction is hydrogenation catalyst A, and the catalyst used in the second stage of reaction is hydrogenation catalyst B. The percentage content $x_1$ of the active metal component in the hydrogenation catalyst A is lower than the percentage content $x_2$ of the active metal component in the hydrogenation catalyst B, preferably $x_1$ is lower than $x_2$ by 0.1-1.5%, more preferably $x_1$ is lower than $x_2$ by 0.3-1.5%. The percentage content $y_1$ of the small crystal size Y zeolite in the hydrogenation catalyst A is higher than the percentage content $y_2$ of the small crystal size Y zeolite in the hydrogenation catalyst B, preferably $y_1$ is higher than $y_2$ by 5-35%, more preferably $y_1$ is higher than $y_2$ by 10-35%. According to the above preferred embodiment, hexadecahydropyrene at higher purity can be obtained, and the yield is higher.

In the method disclosed in the present invention, the conditions of the hydrogenation reaction may be a conventional choice in the prior art. Preferably, the conditions of the hydrogenation reaction include: hydrogen partial pressure of 4-20 MPa; liquid hourly space velocity of 0.05-6 $h^{-1}$; volume ratio of hydrogen to oil of 50-3,000; and average reaction temperature of 150-380° C.

In a further preferred embodiment, in the case that the hydrogenation reaction process consists of two stages of reaction that are executed sequentially, the average reaction temperature in the second stage of reaction is lower than the average reaction temperature in the first stage of reaction by 10-150° C., preferably lower by 30-120° C. More preferably, the average reaction temperature in the first stage of reaction is 180-380° C., further preferably 220-350° C.; the average reaction temperature in the second stage of reaction is 150-350° C., preferably 180-330° C.

In the above preferred embodiment, the first stage of reaction and the second stage of reaction may be executed in the same reactor or in two or more reactors connected in series.

In the present invention, the pyrene compounds are selected from at least one of pyrene and unsaturated hydrogenation products thereof. The unsaturated hydrogenation products of pyrene, for example, may be dihydropyrene, tetrahydropyrene, hexahydropyrene, and octahydropyrene, etc.

In the hydrocarbon oil raw material that contains pyrene compounds, the content of the pyrene compounds may be 0.5 wt % or higher; specifically, for example, the content of the pyrene compounds may be 0.5-10 wt %, such as 0.5 wt %, 0.8 wt %, 1.0 wt %, 1.2 wt %, 1.5 wt %, 2 wt %, 3 wt %, 4 wt %, 5 wt %, 6 wt %, 7 wt %, 8 wt %, 9 wt %, or 10 wt %.

In the present invention, the hydrocarbon oil raw material that contains pyrene compounds may be a conventional hydrocarbon oil raw material in the art, as long as it contains pyrene compounds at a predetermined content. In an embodiment, the hydrocarbon oil raw material that contains pyrene compounds is a heavy distillate having an initial boiling point of 130-220° C., preferably 160-200° C. Preferably, the hydrocarbon oil raw material that contains pyrene compounds is a heavy distillate having an initial boiling point of 130-220° C. and a final boiling point of 300-400° C. Further preferably, the hydrocarbon oil raw material that contains pyrene compounds is a diesel distillate having an initial boiling point of 160-200° C. and a final boiling point of 300-350° C.

According to a preferred embodiment of the present invention, the hydrocarbon oil raw material that contains pyrene compounds is prepared according to the method comprising the following steps:
(1) pretreating coal tar raw material;
(2) hydrofining the pretreated coal tar raw material;
(3) optionally separating the reactor effluent, and then executing a hydrocracking reaction;
(4) treating the reactor effluent obtained through the hydrocracking reaction by gas-liquid separation, then fractionating the separated liquid phase, and taking the fractionated heavy distillate as the hydrocarbon oil raw material that contains pyrene compounds.

The coal tar may be at least one of low-temperature coal tar, medium-temperature coal tar, and high-temperature coal tar, or may be the remaining fraction obtained by extracting at least one of naphthalene, anthracene, phenanthrene, carbazole, and fluoranthene from the coal tar. The aromatic content in the coal tar usually is 20-100 wt %, and the density of the coal tar at 20° C. usually is 1.023-1.235 g/cm$^3$. The distillation range of the coal tar may be any range within 200-700° C., and usually the temperature difference between the final boiling point and the initial boiling point is 100-400° C. Preferably, the coal tar raw material is high-temperature coal tar or the remaining fraction obtained by extracting at least one of anthracene, phenanthrene, carbazole and fluoranthene from the high temperature coal tar.

The pretreatment in the step (1) usually comprises mechanical impurity removal, dehydration, and electrostatic desalting, etc., and may also optional extraction and removal of anthracene and phenanthrene, etc.

The catalyst used in the hydrofining reaction process in the step (2) may be a conventional hydrofining catalyst in the art; for example, the catalyst may be a diesel oil hydrofining catalyst or hydrocracking pretreatment catalyst. The hydrofining catalyst generally has a Group VIB and/or Group VIII metal as the active component and alumina or silicon-containing alumina as the carrier, wherein the Group VIB metal usually is Mo and/or W, and the Group VIII metal usually is Co and/or Ni. Based on the weight of the catalyst, the content of the Group VIB metal measured in oxide is 10-50 wt %, the content of the Group VIII metal measured in oxide is 3-15 wt %; the properties of the catalyst as follows: specific surface area is 100-350 m$^2$/g; pore volume is 0.15-0.6 mL/g. Commercial catalysts that can be selected include hydrofining catalysts 3936, 3996, FF-16, FF-26, FF-36, FF-46, FF-56, FF-66 and the like developed by Sinopec Fushun Research Institute of Petroleum and Petrochemicals, catalysts HC-K and HC-P from UOP, catalysts TK-555 and TK-565 from Topsoe, and catalysts KF-847 and KF-848 from AKZO, etc.

The conditions of the hydrofining reaction in the step (2) generally include: hydrogen partial pressure of 3-19 MPa, average reaction temperature of 260-440° C., liquid hourly space velocity of 0.1-4 h$^{-1}$, and volume ratio of hydrogen to oil of 300:1-3,000:1. The hydrofining in the step (2) may be executed in a conventional reactor in the art, such as fixed bed or fluidized bed, etc. The fixed bed-type reactor may be in a form of up-flow (cocurrent) reactor, down-flow (cocurrent) reactor, or gas-liquid countercurrent reactor.

The catalyst used in the hydrocracking reaction process in the step (3) may be a conventional hydrocracking catalyst in the art, such as light oil hydrocracking catalyst, flexible hydrocracking catalyst, and (high) medium oil hydrocracking catalyst. The hydrocracking catalyst generally has a Group VIB and/or Group VIII metal as the active component, wherein the Group VIB metal usually is Mo and/or W, and the Group VIII metal usually is Co and/or Ni. The carrier of the catalyst may be one or more of alumina, silicon-containing alumina and zeolite. Based on the weight of the catalyst, the content of the Group VIB metal is 10-35 wt % measured in oxide, the content of the Group VIII metal is 3-15 wt % measured in oxide, the content of the zeolite is 5-40 wt %, the content of the alumina is 10-8 wt %; the specific surface area is 100-650 m$^2$/g, and the pore volume is 0.15-0.50 mL/g. Commercial catalysts that can be selected include single-stage hydrocracking catalysts such as FC-26, FC-28, FC-14, ZHC-01, ZHC-02 and ZHC-04 and the like developed by Sinopec Fushun Research Institute of Petroleum and Petrochemicals, hydrocracking catalysts DHC39 and DHC-8 from UOP, and hydrocracking catalyst ICR126 from CHERON, etc, wherein ZHC-02 and ICR126 are hydrocracking catalysts that employ amorphous silica-alumina and Y zeolite as cracking components, and are more suitable for the hydrocracking reaction process in the present invention.

In the present invention, a (high) medium oil hydrocracking catalyst is preferably used. To improve the yield and selectivity of the product, particularly, a medium oil hydrocracking catalyst such as catalyst FC-26 is selected in the present invention. The catalyst achieves a better chain breaking function for alkanes and aromatics that have side chains under the hydrogenation condition, and can break the side chain alkanes in cyclic hydrocarbons, including naphthenic hydrocarbons, side-chain naphthenic hydrocarbons, aromatics, and side-chain aromatics, in the raw material. Besides, the catalyst has a proper saturation function for condensed aromatics without side chain, and hardly has a ring opening function. The oil generated through hydrocracking is fractionated, so as to concentrate the component that contains a precursor of the target product in appropriate narrow fractions. Therefore, the use of medium oil hydrocracking catalysts can maintain the maximum amount of cyclic hydrocarbons in the product, and contributes to an increase in the yield of the final target product.

The reactor used in the hydrocracking system may be a conventional fixed bed hydrogenation reactor, more preferably a down-flow fixed bed reactor. The process conditions of the hydrocracking reaction in the step (3) generally include: hydrogen partial pressure of 3-19 MPa, average reaction temperature of 260-440° C., liquid hourly space velocity of 0.3-4 h$^{-1}$, and volume ratio of hydrogen to oil of 300:1-5,000:1.

In the step (3), the term "optionally" means that the separation procedure, e.g., gas-liquid separation, may be included or not included.

The fractionation operation in the step (4) may adopt a conventional technique in the art. The initial boiling point of the heavy distillate obtained through the fractionation may be 130-220° C., preferably 160-200° C. Preferably, the heavy distillate obtained through the fractionation in the step (4) is diesel distillate; further preferably, the initial boiling point of the diesel distillate is 130-220° C., more preferably 160-200° C.; the final boiling point is 280-400° C., more preferably 300-350° C.

In the present invention, the method may further comprise removing the naphtha fraction from the heavy distillate obtained in the step (4), and then taking the remaining liquid fraction obtained after such operation as the hydrocarbon oil raw material that contains pyrene compounds.

In the present invention, the method may further comprise separating and fractionating the reactor effluent obtained through the hydrogenation reaction to obtain a component rich in hexadecahydropyrene and a heavy component, and returning the heavy component at least partially to the step (3) for hydrocracking reaction. This fractionation process may be executed with a conventional fractionation technique in the art. The products obtained by the fractionation further include a liquid light component, besides the component rich in hexadecahydropyrene belonging to the intermediate component and the heavy component, wherein the cutting temperature of the liquid light component and the intermediate component (component rich in hexadecahydropyrene) is 130-280° C., preferably 200-260° C. The cutting temperature of the intermediate component and the heavy component is 300-360° C., preferably 320-340° C. After the liquid intermediate component is treated by cooling, filtering, vacuum-extraction, and optional centrifugal separation, the obtained solid is a high-purity hexadecahydropyrene product; the purity of the product may be 95 wt % or higher as measured in analysis. In view that the obtained liquid heavy component above the cutting temperature contains pentacyclic hydrocarbons or heavier hydrocarbons, such as dibenzopyrene and indenopyrene, etc., the liquid heavy component may be converted by cyclic hydrocracking into pyrene, so as to improve the yield of the target product.

In the present invention, in order to obtain a high-purity hexadecahydropyrene product, the method further comprises separating and fractionating the reactor effluent obtained through the hydrogenation reaction to obtain a component rich in hexadecahydropyrene and a heavy component, and treating the component rich in hexadecahydropyrene by cooling, filtering, and extraction, to obtain solid hexadecahydropyrene. This fractionation process may be executed with a conventional fractionation technique in the art. The initial boiling point of the liquid distillate rich in hexadecahydropyrene that is obtained through fractionation usually is 220-300° C., preferably 260-280° C.; the final boiling point is generally >300-360° C. (greater than 300° C. and less than or equal to 360° C.), preferably 320-340° C. As the liquid distillate is cooled, the generated hexadecahydropyrene crystalizes and precipitates from the liquid, which is then filtered and optionally separated by centrifugal separation to obtain a high-purity hexadecahydropyrene product.

According to an embodiment of the present invention, the method for preparing hexadecahydropyrene comprises:

(1) pretreating coal tar raw material;
(2) mixing the coal tar obtained in the step (1) with hydrogen, and loading the resultant mixture into a hydrofining reaction zone, so that the mixture contacts with a hydrofining catalyst to react;
(3) optionally separating the hydrofining reactor effluent obtained in the step (2), and feeding the reactor effluent together with hydrogen into a hydrocracking reaction zone, so that the mixture contacts with a hydrocracking catalyst to react;
(4) treating the hydrocracking effluent by gas-liquid separation, and then fractionating the separated liquid to obtain a heavy distillate having an initial boiling point of 130-220° C.;
(5) mixing the heavy distillate obtained in the step (4) with hydrogen, and loading the resultant mixture into a reactor, so that the mixture contacts with the hydrogenation catalyst in the present invention to has a hydrogenation reaction, i.e., supplementary hydrofining reaction;
(6) separating and fractionating the reactor effluent obtained in the step (5) to obtain a component rich in hexadecahydropyrene and a heavy component, and treating the component rich in hexadecahydropyrene by cooling, filtering, and vacuum extraction; the solid obtained in that way is the hexadecahydropyrene product.

Further preferably, the hydrogenation reaction process in the step (5) includes two stages of reaction that are executed sequentially; correspondingly, the catalyst used in the first stage of reaction is hydrogenation catalyst A, and the catalyst used in the second stage of reaction is hydrogenation catalyst B. The percentage content $x_1$ of the active metal component in the hydrogenation catalyst A is lower than the percentage content $x_2$ of the active metal component in the hydrogenation catalyst B, preferably $x_1$ is lower than $x_2$ by 0.1-1.5%, more preferably $x_1$ is lower than $x_2$ by 0.3-1.5%. The percentage content $y_1$ of the small crystal size Y zeolite in the hydrogenation catalyst A is higher than the percentage content $y_2$ of the small crystal size Y zeolite in the hydrogenation catalyst B, preferably $y_1$ is higher than $y_2$ by 5-35%, more preferably $y_1$ is higher than $y_2$ by 10-35%.

The hydrogenation catalyst used in the first stage and the hydrogenation catalystcatalysts used in second stage of the reaction have different properties due to the difference in the content of the active metal component and the content of the small crystal size Y zeolite. The hydrogenation catalyst A has a lower content of active metal component and a higher content of Y zeolite; therefore, the cracking performance of this catalyst is higher The paraffin hydrocarbons and polycyclic aromatic hydrocarbons with side chains that are still contained in the diesel distillate obtained through coal tar hydrocracking further have a contact reaction with the hydrogenation catalyst A, almost all of the side chains on the polycyclic aromatic hydrocarbons are stripped from the aromatic rings through the reaction, and the polycyclic aromatic hydrocarbons have a double-bond saturation reaction partially at the same time; for example, hexahydropyrene can be generated from the coarse pyrene through the hydrogenation. The hydrogenation catalyst B has a higher hydrogenation performance and a weaker cracking activity because of its higher content of active metal component and lower content of small crystal size Y zeolite. When the hydrogenation product obtained in the first stage of reaction has a contact reaction with the hydrogenation catalyst B, the non-perhydropyrene such as hexahydropyrene generated through partial hydrogenation is further hydrogenated, and it has a powerful saturation capability since the cracking activity of the catalyst is limited at a lower reaction temperature; thus, all of the carbon-carbon double bonds are saturated, and thereby a hexadecahydropyrene (perhydropyrene) product is obtained, and the yield of hexadecahydropyrene is improved by the method disclosed in the present invention. Therefore, by means of grading and combination of the hydrogenation catalysts in the hydrogenation reaction process according to the above preferred method, hydrosaturation of the condensed aromatics, especially coarse pyrene, in the diesel distillate is realized, so that the hydrogenation method can be used to directly produce high-purity hexadecahydropyrene products.

Furthermore, compared with the prior art, the method in the specific embodiment described above has the following characteristics:

(1) According to the method disclosed in the present invention, coal tar raw material is used as an initial raw material, and an appropriate process flow is selected, so that high-purity hexadecahydropyrene is prepared through a hydrogenation process, and solvent oil products with excellent performance are also obtained at the same time. The method disclosed in the present invention greatly broadens the potential of producing high value-added products from coal tar. It not only provides a processing method for improving the economic value of low added-value coal tar, but also develops a new raw material and an innovative process route for hexadecahydropyrene product.

(2) In the present invention, first, the hydrofining, hydrocracking and fractionation process are carries out, in view that the aromatic content in the diesel oil obtained through hydrocracking of coal tar is high and a large quantity of light and heavy components in which hexadecahydropyrene is dissolved are generated during the hydrocracking process, a narrow fraction rich in hexadecahydropyrene is fractionated from the oil generated through hydrocracking, hereby enriching the condensed aromatic components with three or more rings into the diesel distillate, and achieving isolation (separation) between the components of the miscible target products, reducing the effect of soluble components on the follow-up supplementary refining reaction; next, the supplementary hydrogenation process is carried out, wherein the selective cracking and hydrogenation capability of a noble metal catalyst that contains small crystal size Y zeolite for condensed aromatics is utilized to achieve complete hydrogenation of tetracyclic aromatic hydrocarbon (coarse pyrene), and thereby distillate oil rich in perhydropyrene (i.e., hexadecahydropyrene) is obtained; finally, the perhydropyrene is enriched through a fractionation process, after cooling, hexadecahydropyrene crystallizes and precipitates from the distillate oil.

(3) The hydrogenation catalyst used in the present invention employs small crystal size Y zeolite as an acidic component. The Y zeolite has the characteristics of high silica-alumina ratio, high crystallinity, a large quantity of secondary pore, and large specific surface area, it cooperates with amorphous silica-alumina and metal components Pt and Pd that have hydrogenation activity, which not only gives better play to the aromatics hydrosaturation activity, but also facilitates the selective ring opening and chain breakage of aromatics, and is beneficial to the diffusion of reaction product, the capacity of carbon tolerance is also greatly improved, thereby increasing the activity, selectivity and stability of the catalyst. This catalyst is particularly suitable for use in the hydrodearomatization reaction of cycloalkyl raw materials, especially a cycloalkyl raw material with high viscosity and high content of condensed aromatics.

(4) In the present invention, preferably two different hydrogenation catalysts are used in the supplementary hydrogenation reaction zone. The hydrogenation catalyst A used in the first stage of reaction has higher Y zeolite content and lower metal content, and therefore exhibits higher cracking activity. For hydrocracked diesel distillate in which the condensed aromatics with three rings or more are enriched, a chain breaking reaction of condensed aromatics with side chain alkanes can be achieved effectively by virtue of the higher cracking activity of the hydrogenation catalyst A, so as to further strip the side chains from the aromatic rings. The hydrogenation catalyst B used in the second stage of reaction has higher hydrogenation activity because of its higher metal content and lower Y zeolite content; in addition, its appropriate cracking activity also plays an important role in hydrosaturation of condensed aromatics. Therefore, the non-perhydropyrene (e.g., hexahydropyrene) that is generated through partial hydrogenation in the first stage of reaction may be completely hydrosaturated on all aromatic rings in the second stage of reaction at a lower reaction temperature, and thereby obtaining a hexadecahydropyrene (perhydropyrene) product.

(5) In the present invention, a processing scheme of mildly and gradually saturating the heterocyclic aromatics in the diesel distillate obtained through hydrocracking is used for production hexadecahydropyrene product and low-aromatic solvent oil, so that condensation, coking and cracking reactions of the aromatics in the diesel distillate produced through coal tar hydrocracking at a high temperature in a single-stage process, which seriously affect the service life of the catalyst, can be avoided as far as possible.

Hereunder the method disclosed in the present invention will be described in more detail below with reference to the accompanying drawings and examples.

Figure 1:
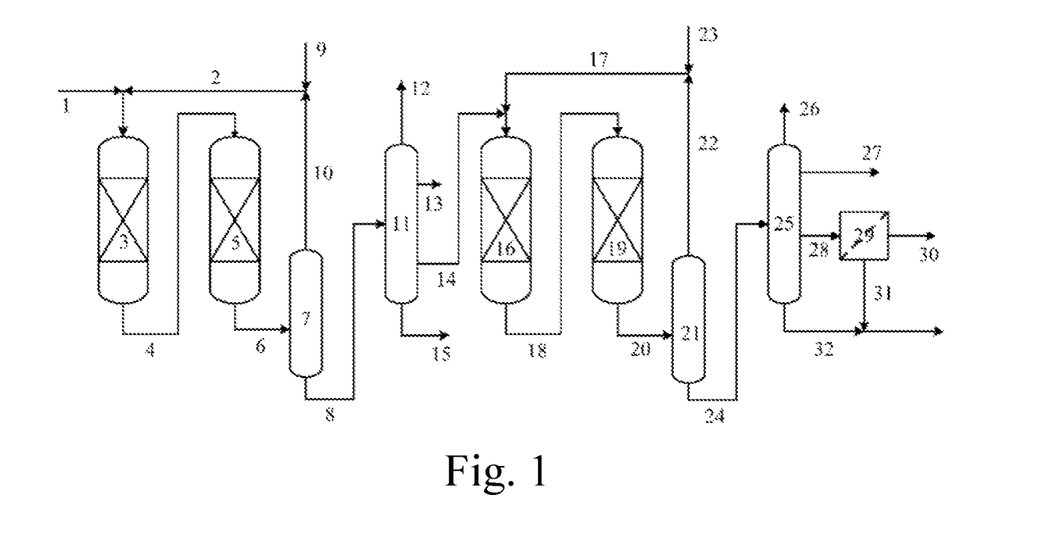
FIG. 1 is a flow diagram of an embodiment of the method for preparing hexadecahydropyrene in the present invention.

As shown in FIG. 1, a process flow in the present invention is as follows: after pretreatment (the pretreatment unit is omitted in the figure), the coal tar flows through a pipeline 1, is mixed with hydrogen flowing through a pipeline 2 and then enters into a hydrofining reactor 3 for hydrogenation reaction including removal of sulfur, nitrogen, oxygen, and metals, etc., the refined reactor effluent enters a hydrocracking reactor 5 via a pipeline 4 for cracking reaction, the hydrocracking reactor effluent enters a gas-liquid separator 7 which usually includes a high-pressure separator and a low-pressure separator via a pipeline 6, the obtained hydrogen-rich gas in the separator flows through a pipeline 10 and is optionally treated to remove hydrogen sulfide, and then is mixed with fresh hydrogen charged through a pipeline 9 to obtain circulating hydrogen. The liquid obtained in the gas-liquid separator enters a fractionating tower 11 via a pipeline 8 for separation, the gas product, light distillate and heavy distillate obtained through the separation are discharged through pipelines 12, 13 and 15 respectively, and the diesel fraction obtained through the separation flows through a pipeline 14 and is mixed with hydrogen charged through a pipeline 17, and then flows into a first supplementary hydrofining reactor 16 and contacts with a low-activity hydrogenation catalyst A therein to have a hydrogenation reaction; the obtained reactor effluent enters a second supplementary hydrofining reactor 19 via a pipeline 18 and contacts with a high-activity hydrogenation catalyst B therein in the presence of hydrogen, so that tetracyclic aromatics and a small amount of tricyclic aromatics are saturated while maintaining the ring-shaped integrity of the resulting cycloalkane after saturation of these polycyclic aromatics, to be converted into cycloalkanes with three or four rings. The effluent obtained through supplementary hydrofining enters a gas-liquid separator 21 which usually includes a high-pressure separator and a low-pressure separator via a pipeline 20 for separation, the hydrogen-rich gas obtained through the separation flows through a pipeline 22 and is mixed with fresh hydrogen introduced through a pipeline 23 to obtain circulating hydrogen; and the liquid obtained through the separation is optionally treated by air stripping (omitted in the figure), and then enters a fractionating tower 25 via a pipeline 24 for fractionation; then, a small amount of gas obtained in the tower is discharged through a pipeline 26, and the obtained liquid rich in hexadecahydropyrene in the tower enters a cooling, filtering, and vacuum extraction unit 29 via a pipeline 28; finally, the resulting solid product, hexadecahydroquinone, is discharged via a pipeline 30; the low-boiling solvent oil obtained through fractionation in the tower flows through a pipeline 27, the high boiling solvent oil flows through a pipeline 32 and then is mixed with the liquid that flows through a pipeline 31 after extraction to obtain a mixture taken as a low-aromatic solvent oil product.

Figure 2:
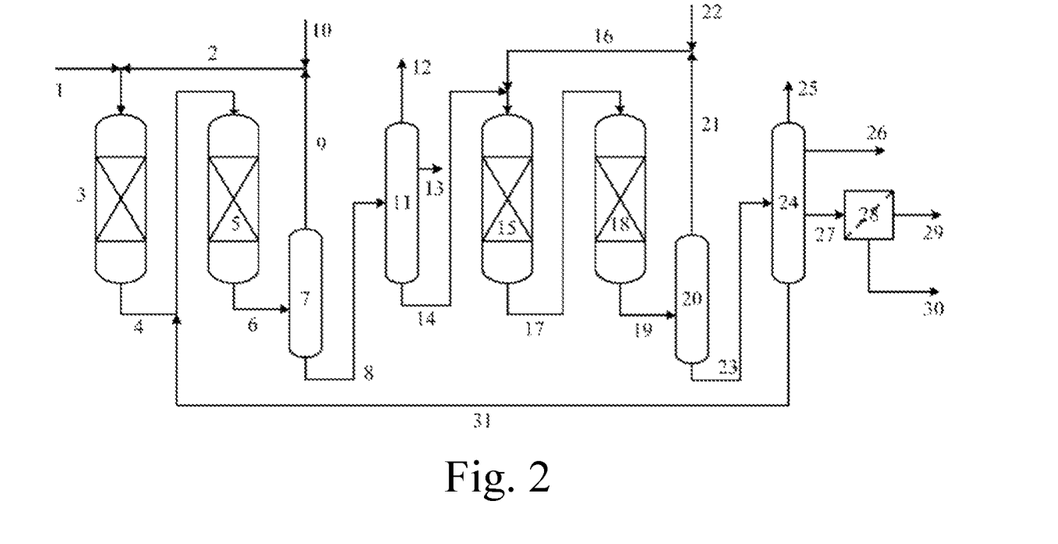
FIG. 2 is a flow diagram of another embodiment of the method for preparing hexadecahydropyrene in the present invention.

As shown in FIG. 2, another process flow in the present invention is as follows: after pretreatment (the pretreatment unit is omitted in the figure), the coal tar flows through a pipeline 1, is mixed with hydrogen flowing through a pipeline 2 and then enters into a hydrofining reactor 3 for hydrogenation reaction including removal of sulfur, nitrogen, oxygen, and metals, etc., the refined reactor effluent enters a hydrocracking reactor 5 via a pipeline 4 for cracking reaction, the hydrocracking reactor effluent enters a gas-liquid separator 7 which usually includes a high-pressure separator and a low-pressure separator via a pipeline 6, the obtained hydrogen-rich gas in the separator flows through a pipeline 9 and is optionally treated to remove hydrogen sulfide, and then is mixed with fresh hydrogen charged through a pipeline 10 to obtain circulating hydrogen. The liquid obtained in the gas-liquid separator enters a fractionating tower 11 via a pipeline 8 for separation, the gas product and light distillate obtained through the separation are discharged through pipelines 12 and 13 respectively, the heavy distillate obtained through the separation flows through a pipeline 14 and is mixed with hydrogen charged through a pipeline 16, and then flows into a first supplementary hydrofining reactor 15 and contacts with a low-activity hydrogenation catalyst A therein to have a hydrogenation reaction; the obtained reactor effluent enters a second supplementary hydrofining reactor 18 via a pipeline 17 and contacts with a high-activity hydrogenation catalyst B therein in the presence of hydrogen, so that tetracyclic aromatics and a small amount of tricyclic aromatics are saturated while maintaining the ring-shaped integrity of the resulting cycloalkanes after saturation of these polycyclic aromatics, to be converted into cycloalkanes with three or four rings. The effluent obtained through supplementary hydrofining enters a gas-liquid separator 20 which usually includes a high-pressure separator and a low-pressure separator via a pipeline 19 for separation, the hydrogen-rich gas obtained through the separation flows through a pipeline 21 and is mixed with fresh hydrogen introduced through a pipeline 22 to obtain circulating hydrogen; and the liquid obtained through the separation is optionally treated by air stripping (omitted in the figure), and then enters a fractionating tower 24 via a pipeline 23 for fractionation; then, a small amount of gas obtained in the tower is discharged through a pipeline 25, and the liquid rich in hexadecahydropyrene obtained in the tower enters a cooling, filtering, and vacuum extraction unit 28 via a pipeline 27; finally, the resulting solid product, hexadecahydropyrene, is discharged via a pipeline 29; the low-boiling solvent oil obtained through fractionation in the tower flows through a pipeline 26 and is mixed with the liquid discharged through a pipeline 30 after extraction to obtain a mixture taken as a low-aromatic solvent oil product; the high boiling solvent oil obtained in the tower is returned to the hydrocracking reactor 5 via a pipeline 31 for cracking reaction to obtain more hexadecahydropyrene component.

In the present invention, the purity of the hexadecahydropyrene detected by gas chromatography-mass spectrometry (GC-MS) small molecule qualitative analysis, the Saybolt color of the solvent oil is detected with the method specified in GB/T3555-1992, the aromatic content in the solvent oil is detected with the method specified in GB/T 17474, and the content of pyrene compounds in the product obtained through coal tar hydrocracking is measured with the method specified in ISO13877-1998.

The high-temperature coal tar raw material used in the following examples and comparative examples is shown in the following Table 1. The high-temperature coal tar is coal tar distillate obtained by treating the coal, produced in Anyang City, Henan Province, through dry distillation at 1000° C. and naphthalene removal.

TABLE 1

|  | High-temperature coal tar |
|---|---|
| Density (20° C.)/kg · cm$^{-3}$ | 1023.1 |
| Distillation range, ° C. | 320-550 |
| Aromatic content, wt % | 52.3 |
| Aromatics with three or more rings, wt % | 43 |
| Hexadecahydropyrene, wt % | 0 |
| Solidifying point, ° C. | 32 |
| Sulfur, μg/g | 3000 |
| Nitrogen, μg/g | 15000 |

The supplementary hydrofining catalysts used in the following examples are prepared by the method disclosed in CN104588073A. Specifically, the properties of the supplementary hydrofining catalysts are shown in Table 2.

TABLE 2

| Item | Catalyst A | Catalyst B |
|---|---|---|
| Active metal, wt % | | |
| Pt/Pd | 0.12/0.28 | 0.25/0.55 |
| Carrier | Amorphous silica-alumina + alumina + Y zeolite | Amorphous silica-alumina + alumina + Y zeolite |
| Y zeolite, wt % | 30 | 16 |
| Properties of Y zeolite | | |
| Average grain diameter, nm | 370 | 370 |
| Relative crystallinity, % | 110 | 110 |
| Secondary pores (1.7-10 nm), % | 62 | 62 |
| Molar ratio of SiO$_2$/Al$_2$O$_3$ | 85 | 85 |
| Lattice constant, nm | 2.432 | 2.432 |
| Specific surface area, m$^2$/g | 990 | 990 |
| Pore volume, mL/g | 0.59 | 0.59 |

The supplementary hydrofining catalysts used in the following comparative examples are prepared by the method specified in CN104588073A, wherein the small crystal size Y zeolite is prepared with reference to the comparative examples 1 and 2 in CN104588073A. Specifically, the properties of the supplementary hydrofining catalysts are shown in the following Table 3.

TABLE 3

| Item | Catalyst C | Catalyst D |
|---|---|---|
| Active metal, wt % | | |
| Pt/Pd | 0.12/0.28 | 0.25/0.55 |
| Carrier | Amorphous silica-alumina + alumina + Y zeolite | Amorphous silica-alumina + alumina + Y zeolite |
| Y zeolite, wt % | 30 | 16 |
| Properties of Y zeolite | | |
| Average grain diameter, nm | 400 | 450 |
| Relative crystallinity, % | 95 | 80 |
| Secondary pores (1.7-10 nm), % | 37.1 | 27.5 |
| Molar ratio of $SiO_2/Al_2O_3$ | 50 | 25 |
| Lattice constant, nm | 2.441 | 2.450 |
| Specific surface area, $m^2/g$ | 892 | 780 |
| Pore volume, mL/g | 0.33 | 0.32 |

The operating conditions of the hydrofining reaction and hydrocracking reaction in the following examples 1-4 and comparative examples 1-3 are shown in the following Table 4.

TABLE 4

| | Hydrofining | Hydrocracking |
|---|---|---|
| Catalyst | FF-36 | FC-26 |
| Hydrogen partial pressure, MPa | 15.0 | 15.0 |
| LHSV, $h^{-1}$ | 0.6 | 0.6 |
| Volume ratio of hydrogen to oil, v/v | 1500 | 1500 |
| Reaction temperature, °C. | 340 | 360 |
| Nitrogen content, μg/g | 12 | 5 |

In the following examples 1-4 and comparative examples 1-3, the distillation range of the diesel distillate separated from the hydrocracking reactor effluent is 160-340° C., and the product distribution of the hydrocracking reaction products includes: <160° C. fraction: 8.3 wt %, 160-340° C. fraction: 55.5 wt %, >340° C. fraction: 36.2 wt %, and the pyrene content in the 160-340° C. fraction is 1.5 wt %; the distillation range of the fluid fraction rich in hexadecahydropyrene that is separated from the supplementary hydrofining reactor effluent is 280-320° C.

Example 1

The process shown in FIG. 1 is used, wherein the catalyst in the supplementary hydrofining reaction zone is not sectioned, and only the catalyst A is used instead, wherein the operating conditions of the supplementary hydrofining reaction zone and the yield and purity of the obtained hexadecahydropyrene are shown in Table 5.

Comparative Example 1

Referring to Example 1, but the difference is that the catalyst used in the supplementary hydrofining reaction zone is catalyst C, wherein the operating conditions of the supplementary hydrofining reaction zone and the yield and purity of the obtained hexadecahydropyrene are shown in Table 5.

Example 2

The process shown in FIG. 1 is used, wherein the catalyst in the supplementary hydrofining reaction zone is not sectioned, and only the catalyst B is used instead, wherein the operating conditions of the supplementary hydrofining reaction zone and the yield and purity of the obtained hexadecahydropyrene are shown in Table 5.

Comparative Example 2

Referring to Example 2, but the difference is that the catalyst used in the supplementary hydrofining reaction zone is catalyst D, wherein the operating conditions of the supplementary hydrofining reaction zone and the yield and purity of the obtained hexadecahydropyrene are shown in Table 5.

Example 3

The process shown in FIG. 1 is used, wherein the supplementary hydrofining reaction zone is divided into two supplementary hydrofining reaction stages, and a grading scheme of catalyst A and catalyst B is used, specifically, the catalyst A is used in the first supplementary hydrofining reaction stage, and the catalyst B is used in the second supplementary hydrofining reaction stage, wherein the operating conditions of the supplementary hydrofining reaction zone and the yield and purity of the obtained hexadecahydropyrene are shown in Table 5.

Comparative Example 3

Referring to Example 3, but the difference is that the catalyst grading scheme used in the supplementary hydrofining reaction zone is catalyst C and catalyst D, specifically, the catalyst C is used in the first supplementary hydrofining reaction stage, and the catalyst D is used in the second supplementary hydrofining reaction stage, wherein the operating conditions of the supplementary hydrofining reaction zone and the yield and purity of the obtained hexadecahydropyrene are shown in Table 5.

Example 4

Referring to Example 3, but the difference is that the grading sequence of the supplementary hydrofining catalysts is changed, i.e., the catalyst B is used in the first supplementary hydrofining reaction stage, and the catalyst A is used in the second supplementary hydrofining reaction stage, wherein the operating conditions of the supplementary hydrofining reaction zone and the yield and purity of the obtained hexadecahydropyrene are shown in Table 5.

TABLE 5

| | Example 1 | Comparative Example 1 | Example 2 | Comparative Example 2 | Example 3 | Comparative Example 3 | Example 4 |
|---|---|---|---|---|---|---|---|
| Conditions in the first supplementary hydrofining reaction stage | | | | | | | |
| Reaction temperature, °C. | 280 | 280 | — | — | 280 | 280 | 220 |
| Hydrogen partial pressure, MPa | 15.0 | 15.0 | — | — | 15.0 | 15.0 | 15.0 |
| Volume ratio of hydrogen to oil, v/v | 1000 | 1000 | — | — | 1000 | 1000 | 1000 |
| LHSV, $h^{-1}$ | 0.5 | 0.5 | — | — | 0.5 | 0.5 | 0.5 |
| Conditions in the second supplementary hydrofining reaction stage | | | | | | | |
| Reaction temperature, °C. | — | — | 220 | 220 | 220 | 220 | 280 |
| Hydrogen partial pressure, MPa | — | — | 15.0 | 15.0 | 15.0 | 15.0 | 15.0 |
| Volume ratio of hydrogen to oil, v/v | — | — | 1000 | 1000 | 1000 | 1000 | 1000 |
| LHSV, $h^{-1}$ | — | — | 0.5 | 0.5 | 0.5 | 0.5 | 0.5 |
| Product properties Hexadecahydropyrene | | | | | | | |
| Yield[1], % | 0.6 | 0.2 | 0.4 | 0.1 | 1.4 | 0.3 | 0.08 |
| Density (20° C.)/kg · $m^{-3}$ | 979.1 | 978.5 | 975.0 | 976.1 | 971.1 | 973.2 | 977.0 |
| Flash point, °C. | 123.5 | 123.3 | 123.6 | 123.9 | 124.1 | 124.3 | 123.3 |
| Purity, % | >85 | >82 | >83 | >80 | >99 | >85 | >90 |
| Solvent oil | | | | | | | |
| Yield[1], % | 99.4 | 97.3 | 98.3 | 97.5 | 97.3 | 97.4 | 98.2 |
| Density (20° C.)/kg · $m^{-3}$ | 895.3 | 898.2 | 906.1 | 911.5 | 888.3 | 898.9 | 889.5 |
| Sulfur/nitrogen, μg/g | 2.0/1.0 | 2.0/1.0 | 2.0/1.0 | 2.0/1.0 | 2.0/1.0 | 2.0/1.0 | 2.0/1.0 |
| Solidifying point, °C. | −48 | −48 | −50 | −48 | −45 | −48 | −46 |
| Saybolt color, no. | +20 | +20 | +15 | +13 | +30 | +20 | +30 |
| Aromatic content, wt % | 2.3 | 4.1 | 6.5 | 7.5 | 0.001 | 3.6 | 0.001 |

[1] Based on 160-340° C. fraction.

It can be seen from the data listed in Table 5 that, for the raw material hydrogenation solution in the prior art, the purity and yield of the hexadecahydropyrene products obtained under different conditions are different, and the catalyst grading scheme in Example 3 is optimal.

It is seen from the data of the examples 1-4, with the processing method of pretreatment, hydrofining, hydrocracking, and supplement hydrofining of the coal tar raw material in the present invention, a high-purity hexadecahydropyrene product can be obtained. Moreover, wherein a catalyst grading scheme is used in the supplementary refining reaction zone, the yield and purity of the obtained hexadecahydropyrene are higher, and a more ideal hydrogenation effect is attained.

The operating conditions of the hydrofining reaction and hydrocracking reaction in the following examples 5-8 and comparative examples 4-6 are shown in the following Table 6.

TABLE 6

| | Hydrofining | Hydrocracking |
|---|---|---|
| Catalyst | FF-36 | FC-26 |
| Hydrogen partial pressure, MPa | 15.0 | 15.0 |
| LHSV, $h^{-1}$ | 0.6 | 0.6 |
| Volume ratio of hydrogen to oil, v/v | 2000 | 2000 |
| Reaction temperature, °C. | 335 | 365 |
| Nitrogen content, μg/g | 11 | 3 |

In the following examples 5-8 and comparative examples 4-6, the initial boiling point of the heavy distillate separated from the hydrocracking reactor effluent is 160° C., the product distribution of the products obtained through hydrocracking reaction include: <160° C. fraction 8.4 wt %, ≥160° C. fraction 91.6 wt %, and the pyrene content in the ≥160° C. fraction is 1.2 wt %; the distillation range of the fluid fraction rich in hexadecahydropyrene separated from the supplementary hydrofining reactor effluent is 250-340° C.

Example 5

The process shown in FIG. 2 is used, wherein the catalyst in the supplementary hydrofining reaction zone is not sectioned, and only the catalyst A is used instead, wherein the operating conditions of the supplementary hydrofining reaction zone and the yield and purity of the obtained hexadecahydropyrene are shown in Table 7.

Comparative Example 4

Referring to Example 5, but the difference is that the catalyst used in the supplementary hydrofining reaction zone is catalyst C, wherein the operating conditions of the supplementary hydrofining reaction zone and the yield and purity of the obtained hexadecahydropyrene in the example are shown in Table 7.

Example 6

The process shown in FIG. 2 is used, wherein the catalyst in the supplementary hydrofining reaction zone is not sectioned, and only the catalyst B is used instead, wherein the operating conditions of the supplementary hydrofining reaction zone and the yield and purity of the obtained hexadecahydropyrene are shown in Table 7.

Comparative Example 5

Referring to Example 6, but the difference is that the catalyst used in the supplementary hydrofining reaction zone is catalyst D, wherein the operating conditions of the supplementary hydrofining reaction zone and the yield and purity of the obtained hexadecahydropyrene are shown in Table 7.

Example 7

The process shown in FIG. 2 is used, wherein the supplementary hydrofining reaction zone is divided into two supplementary hydrofining reaction stages, and a grading scheme of catalyst A and catalyst B is used, specifically, the catalyst A is used in the first supplementary hydrofining reaction stage, and the catalyst B is used in the second supplementary hydrofining reaction stage, wherein the operating conditions of the supplementary hydrofining reaction zone and the yield and purity of the obtained hexadecahydropyrene are shown in Table 7.

Comparative Example 6

Referring to Example 7, but the difference is that the catalyst grading scheme used in the supplementary hydrofining reaction zone is catalyst C and catalyst D, specifically, the catalyst C is used in the first supplementary hydrofining reaction stage, and the catalyst D is used in the second supplementary hydrofining reaction stage, wherein the operating conditions of the supplementary hydrofining reaction zone and the yield and purity of the obtained hexadecahydropyrene are shown in Table 7.

Example 8

Referring to Example 7, but the difference is that the grading sequence of the supplementary hydrofining catalysts is changed, i.e., the catalyst B is used in the first supplementary hydrofining reaction stage, and the catalyst A is used in the second supplementary hydrofining reaction stage, wherein the operating conditions of the supplementary hydrofining reaction zone and the yield and purity of the obtained hexadecahydropyrene are shown in Table 7.

It can be seen from the data listed in Table 7 that, for the raw material hydrogenation solution in the prior art, the purity and yield of the hexadecahydropyrene products obtained under different conditions are different, and the catalyst grading scheme in Example 7 is optimal.

It is seen from the data of the examples 5-8 that, with the processing method of pretreatment, hydrofining, hydrocracking, and supplement hydrofining of the coal tar raw material in the present invention, a high-purity hexadecahydropyrene product can be obtained. Moreover, wherein a catalyst grading scheme is used in the supplementary refining reaction zone, the yield and purity of the obtained hexadecahydropyrene are higher, and a more ideal hydrogenation effect is attained.

While the present invention is described above in detail in some preferred embodiments, the present invention is not limited to those embodiments. Various simple variations, including combinations of the technical features in any other appropriate way, can be made to the technical scheme of the present invention within the scope of the technical concept of the present invention, but such variations and combinations shall be deemed as disclosed content in the present invention and falling in the protection scope of the present invention.

The invention claimed is:

1. A method for preparing hexadecahydropyrene, comprising:
   hydrogenating a hydrocarbon oil raw material that contains pyrene compounds in the presence of a first hydrogenation catalyst in a first reactor;
   hydrogenating an effluent from the first reactor in the presence of a second hydrogenation catalyst in a second reactor;

TABLE 7

| | Example 5 | Comparative Example 4 | Example 6 | Comparative Example 5 | Example 7 | Comparative Example 6 | Example 8 |
|---|---|---|---|---|---|---|---|
| Conditions in the first supplementary hydrofining reaction stage | | | | | | | |
| Reaction temperature, °C. | 282 | 282 | — | — | 282 | 282 | 225 |
| Hydrogen partial pressure, MPa | 15.0 | 15.0 | — | — | 15.0 | 15.0 | 15.0 |
| Volume ratio of hydrogen to oil, v/v | 1000 | 1000 | — | — | 1000 | 1000 | 1000 |
| LHSV, $h^{-1}$ | 0.5 | 0.5 | — | — | 0.5 | 0.5 | 0.5 |
| Conditions in the second supplementary hydrofining reaction stage | | | | | | | |
| Reaction temperature, °C. | — | — | 223 | 223 | 223 | 223 | 283 |
| Hydrogen partial pressure, MPa | — | — | 15.0 | 15.0 | 15.0 | 15.0 | 15.0 |
| Volume ratio of hydrogen to oil, v/v | — | — | 1000 | 1000 | 1000 | 1000 | 1000 |
| LHSV, $h^{-1}$ | — | — | 0.5 | 0.5 | 0.5 | 0.5 | 0.5 |
| Product properties Hexadecahydropyrene | | | | | | | |
| Yield [2], % | 0.5 | 0.2 | 0.3 | 0.1 | 1.2 | 0.3 | 0.05 |
| Density (@20° C.)/kg · $cm^{-3}$ | 978.7 | 975.3 | 975.6 | 976.6 | 972.0 | 977.2 | 976.8 |
| Flash point, °C. | 123.7 | 123.3 | 123.4 | 123.5 | 124.2 | 124.5 | 124.0 |
| Purity, wt % | >84 | >80 | >84 | >80 | >98 | >82 | >90 |
| Low-aromatic solvent oil | | | | | | | |
| Yield [2], % | 92.2 | 91.1 | 92.8 | 91.5 | 95.1 | 92.5 | 94.2 |
| Density (@20° C.)/kg · $cm^{-3}$ | 896.0 | 897.6 | 905.8 | 906.5 | 889.1 | 887.3 | 889.3 |
| Sulfur/nitrogen, μg/g | 1.5/1.0 | 1.5/1.0 | 1.5/1.0 | 2.0/1.0 | 1.0/1.0 | 1.5/1.0 | 2.0/1.0 |
| Solidifying point, °C. | −48 | −48 | −49 | −46 | −45 | −45 | −45 |
| Saybolt color, no. | +18 | +16 | +16 | +16 | +30 | +20 | +30 |
| Aromatic content, wt % | 2.0 | 4.5 | 5.9 | 6.8 | 0.001 | 3.5 | 0.001 |

[2] Based on >160° C. fraction.

separating an effluent from the second reactor to obtain a product stream comprising hexadecahydropyrene;

cooling the product stream; and separating hexadecahydropyrene from the cooled product stream, wherein the pyrene compounds are selected from at least one of pyrene and unsaturated hydrogenation products thereof, wherein each of the first hydrogenation catalyst and the second hydrogenation catalyst comprises a carrier and an active metal component loaded on the carrier, wherein the active metal component is Pt, Pd, or Pt and Pd, the carrier comprises a small crystal size Y zeolite, alumina, and amorphous silica-alumina, wherein the small crystal size Y zeolite has an average grain diameter of 200-700 nm, a molar ratio of $SiO_2/Al_2O_3$ of 40-120, a relative crystallinity of ≥95%, a specific surface area of 900-1,200 $m^2/g$, and a pore volume of secondary pores having 1.7-10 nm in diameter that accounts for 50% or more of a total pore volume, and wherein a weight percentage of the active metal component in the first hydrogenation catalyst ($x_1$) is lower than a weight percentage of the active metal component in the second hydrogenation catalyst ($x_2$), and a weight percentage of the small crystal size Y zeolite in the first hydrogenation catalyst ($y_1$) is higher than a weight percentage of the small crystal size Y zeolite in the second hydrogenation catalyst ($y_2$), wherein $x_1$ and $y_1$ are based on a total weight of the first hydrogenation catalyst, and $x_2$ and $y_2$ are based on a total weight of the second hydrogenation catalyst.

2. The method according to claim 1, wherein the average grain diameter of the small crystal size Y zeolite is 300-500 nm, the relative crystallinity is 95-120%, and the pore volume of secondary pores having 1.7-10 nm in diameter accounts for 50-80% of the total pore volume.

3. The method according to claim 1, wherein the small crystal size Y zeolite has a lattice constant of 2.425-2.435 nm and a pore volume of 0.5-0.8 mL/g.

4. The method according to claim 1, wherein both $x_1$ and $x_2$ are in a range of 0.1-2 wt %.

5. The method according to claim 1, wherein ($x_2-x_1$) is in a range of 0.1-1.5%, and ($y_1-y_2$) is in a range of 5-35%.

6. The method according to claim 5, wherein ($x_2-x_1$) is in a range of 0.3-1.5%, and ($y_1-y_2$) is in a range of 10-35%.

7. The method according to claim 1, wherein conditions of the first reactor and the second reactor include: a partial pressure of hydrogen of 4-20 MPa; a liquid hourly space velocity of 0.05-6 $h^{-1}$; a volume ratio of hydrogen to oil of 50-3,000; and an average reaction temperature of 150-380° C.

8. The method according to claim 1, wherein the average reaction temperature in the second reactor is lower than the average reaction temperature in the first reactor by 10-150° C.

9. The method according to claim 8, wherein the average reaction temperature in the first reactor is 180-380° C., and the average reaction temperature in the second reactor is 150-350° C.

10. The method according to claim 1, wherein a content of the pyrene compounds in the hydrocarbon oil raw material is 0.5 wt % or more.

11. The method according to claim 1, wherein the hydrocarbon oil raw material is a heavy distillate oil having an initial boiling point of 130-220° C. and a final boiling point of 300-400° C.

12. The method according to claim 11, wherein the hydrocarbon oil raw material is a diesel distillate having an initial boiling point of 160-200° C. and a final boiling point of 300-350° C.

13. The method according to claim 1, further comprising preparing the hydrocarbon oil raw material through a plurality of steps that comprise:
(1) pretreating a coal tar raw material;
(2) hydrofining the pretreated coal tar raw material;
(3) hydrocracking an effluent from the hydrofining reaction;
(4) separating an effluent from the hydrocracking reaction to obtain a liquid phase and a gas phase, then fractionating the liquid phase to obtain a fractionated heavy distillate, and using the fractionated heavy distillate as the hydrocarbon oil raw material.

14. The method according to claim 13, wherein the coal tar raw material has an aromatic content of 20-100 wt %, a density of 1.023-1.235 $g/cm^3$ at 20° C., and a distillation range of 200-700° C.

15. The method according to claim 13, wherein the coal tar raw material is a high-temperature coal tar or a remaining fraction obtained by extracting at least one of anthracene, phenanthrene, carbazole and fluoranthene from the high-temperature coal tar.

16. The method according to claim 13, wherein step (1) includes pretreating the coal tar raw material by mechanical impurity removal, dehydration, and electrostatic desalting.

17. The method according to claim 13, wherein conditions of the hydrofining reaction include: a hydrogen partial pressure of 3-19 MPa, an average reaction temperature of 260-440° C., a liquid hourly space velocity of 0.1-4 $h^{-1}$, and a volume ratio of hydrogen to oil of 300:1-3,000:1.

18. The method according to claim 13, wherein conditions of the hydrocracking reaction include: a hydrogen partial pressure of 3-19 MPa, an average reaction temperature of 260-440° C., a liquid hourly space velocity of 0.3-4 $h^{-1}$, and a volume ratio of hydrogen to oil of 300:1-5,000:1.

19. The method according to claim 1, wherein separating hexadecahydropyrene from the cooled product stream comprises filtration and extraction.

20. The method according to claim 1, wherein, in the first hydrogenation catalyst and the second hydrogenation catalysts, based on a total weight of the carrier, a content of the small crystal size Y zeolite is 5-40 wt %, a content of the alumina is 10-40 wt %, and a content of the amorphous silica-alumina is 20-65 wt %.

21. The method according to claim 1, wherein a yield of hexadecahydropyrene is 0.3% to 1.4%.

22. The method according to claim 1, wherein a purity of hexadecahydropyrene is 98% or higher.

* * * * *